US00PP25119P2

(12) United States Plant Patent
Miedema-Jorna

(10) Patent No.: US PP25,119 P2
(45) Date of Patent: Nov. 25, 2014

(54) **NEW GUINEA *IMPATIENS* PLANT NAMED 'FIDIMPMAXRED'**

(50) Latin Name: *Impatiens hawkeri*
Varietal Denomination: Fidimpmaxred

(71) Applicant: Anita Miedema-Jorna, De Lier (NL)

(72) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 118 days.

(21) Appl. No.: 13/694,668

(22) Filed: Dec. 21, 2012

(51) Int. Cl.
*A01H 5/00* (2006.01)

(52) U.S. Cl.
USPC ..... Plt./318.6

(58) Field of Classification Search
USPC ..... Plt./318.2, 318.5, 318.6
See application file for complete search history.

*Primary Examiner* — Wendy C Haas
(74) *Attorney, Agent, or Firm* — C. A. Whealy

(57) ABSTRACT

A new and distinct cultivar of *Impatiens* plant named 'Fidimpmaxred', characterized by its upright and broadly outwardly spreading growth habit; mounded plant form; freely branching habit; dark green-colored leaves; early and freely flowering habit; large intense red-colored flowers; and good garden performance.

1 Drawing Sheet

Botanical designation: *Impatiens hawkeri*.
Cultivar denomination: 'FIDIMPMAXRED'.

BACKGROUND OF THE INVENTION

The present invention relates to a new and distinct cultivar of New Guinea *Impatiens* plant, botanically known as *Impatiens hawkeri* and hereinafter referred to by the name 'Fidimpmaxred'.

The new *Impatiens* plant is a product of a planned breeding program conducted by the Inventor in De Lier, The Netherlands. The objective of the breeding program is to create new freely-branching New Guinea *Impatiens* plants with early and freely flowering habit and large uniquely-colored attractive flowers.

The new *Impatiens* plant originated from a cross-pollination made in 2007 by the Inventor in De Lier, The Netherlands of a proprietary selection of *Impatiens hawkeri* identified as code number AMI 081270, not patented, as the female, or seed, parent with a proprietary selection of *Impatiens hawkeri* identified as code number AMI 081280, not patented, as the male, or pollen, parent. The new *Impatiens* plant was discovered and selected by the Inventor as a single flowering plant within the progeny of the stated cross-pollination in a controlled greenhouse environment in De Lier, The Netherlands in 2008.

Asexual reproduction of the new *Impatiens* plant by vegetative cuttings in a controlled environment in De Lier, The Netherlands since 2008 has shown that the unique features of this new *Impatiens* plant are stable and reproduced true to type in successive generations.

SUMMARY OF THE INVENTION

Plants of the new *Impatiens* plant have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Fidimpmaxred'. These characteristics in combination distinguish 'Fidimpmaxred' as a new and distinct *Impatiens* plant:

1. Upright and broadly outwardly spreading growth habit; mounded plant form.
2. Freely branching habit.
3. Dark green-colored leaves.
4. Early and freely flowering habit.
5. Large intense red-colored flowers.
6. Good garden performance.

Plants of the new *Impatiens* can be compared to plants of the parent selections. Plants of the new *Impatiens* differ primarily from plants of the parent selections in the following characteristics:

1. Plants of the new *Impatiens* are more vigorous than plants of the parent selections.
2. Flowers of plants of the new *Impatiens* are larger than flowers of plants of the parent selections.

Plants of the new *Impatiens* can be compared to plants of *Impatiens hawkeri* 'Tamar Red', not patented. In side-by-side comparisons conducted in De Lier, The Netherlands, plants of the new *Impatiens* differed primarily from plants of 'Tamar Red' in the following characteristics:

1. Plants of the new *Impatiens* were more vigorous than plants of 'Tamar Red'.
2. Flowers of plants of the new *Impatiens* were larger than flowers of plants of 'Tamar Red'.

BRIEF DESCRIPTION OF THE PHOTOGRAPH

The accompanying colored photograph illustrates the overall appearance of the new *Impatiens* plant showing the colors as true as it is reasonably possible to obtain in colored reproductions of this type. Colors in the photograph may differ slightly from the color values cited in the detailed botanical description which accurately describe the colors of the new *Impatiens* plant.

The photograph comprises a top perspective view of a typical flowering plant of 'Fidimpmaxred' grown in a container.

DETAILED BOTANICAL DESCRIPTION

The aforementioned photograph and following observations, measurements and values describe plants grown in 19-cm containers in a glass-covered greenhouse in De Lier, The Netherlands under cultural practices typical of commercial *Impatiens* production. During the production of the plants, day and night temperatures averaged 18° C. Plants were eleven weeks old when the photograph and description were taken. In the following description, color references are made to The Royal Horticultural Society Colour Chart, 2007 Edition, except where general terms of ordinary dictionary significance are used.

Botanical classification: *Impatiens hawkeri* 'Fidimpmaxred'.

Parentage:

*Female, or seed, parent*.—Proprietary selection of *Impatiens hawkeri* identified as code number AMI 081270, not patented.

*Male, or pollen, parent*.—Proprietary selection of *Impatiens hawkeri* identified as code number AMI 081280, not patented.

Propagation:

*Type*.—By vegetative cuttings.

*Time to initiate roots, summer*.—About five to seven days at temperatures ranging from 19° C. to 20° C.

*Time to initiate roots, winter*.—About six to eight days at temperatures ranging from 19° C. to 20° C.

*Time to produce a rooted young plant, summer*.—About 14 to 19 days at temperatures ranging from 19° C. to 20° C.

*Time to produce a rooted young plant, winter*.—About 14 to 21 days at temperatures ranging from 19° C. to 20° C.

*Root description*.—Fine; white to brown in color.

*Rooting habit*.—Freely branching.

Plant description:

*Plant and growth habit*.—Upright and broadly outwardly spreading growth habit; mounded plant form, flattened globular; freely branching habit with about five lateral branches; pinching is typically not required; moderately vigorous growth habit.

*Plant height*.—About 32 cm.

*Plant diameter*.—About 48 cm.

Lateral branch description:

*Length*.—About 29 cm.

*Diameter*.—About 1 cm.

*Internode length*.—About 4 cm to 6 cm.

*Strength*.—Moderately strong.

*Aspect*.—Initially upright to outwardly spreading.

*Texture*.—Smooth, glabrous.

*Color*.—Close to 146C heavily tinted with close to 183B.

Foliage description:

*Arrangement*.—Opposite or in whorls of about five; simple.

*Length*.—About 13 cm.

*Width*.—About 5 cm.

*Shape*.—Ovate.

*Apex*.—Acute.

*Base*.—Attenuate.

*Margin*.—Serrate with ciliation.

*Texture, upper and lower surfaces*.—Smooth, glabrous; leathery; moderately glossy in luster.

*Venation pattern*.—Pinnate; arcuate.

*Color*.—Developing leaves, upper surface: Close to 137A. Developing leaves, lower surface: Close to 138B. Fully expanded leaves, upper surface: Darker than N137A; venation, close to 138B. Fully expanded leaves, lower surface: Close to 138B; venation, close to 183D.

*Petiole*.—Length: About 3.5 cm. Diameter: About 3 mm. Texture, upper and lower surfaces: Smooth, glabrous. Color, upper and lower surfaces: Close to 147D heavily tinted with close to 183D.

Flower description:

*Flower type and flowering habit*.—Single rounded axillary flowers; freely flowering habit with about 25 flowers developing per plant; flowers positioned above the foliage and typically face upright or outwardly.

*Fragrance*.—None detected.

*Natural flowering season*.—Year-round under greenhouse conditions; in the garden, continuous flowering from spring through the summer in The Netherlands; early flowering habit, plants begin flowering about ten to eleven weeks after planting.

*Flower longevity*.—Flowers last about ten days on the plant under greenhouse conditions; petals self-cleaning, gynoecium persistent.

*Flower size*.—Diameter: About 7 cm. Depth: About 5 mm.

*Flower buds*.—Length: About 2 cm. Diameter: About 1.5 cm. Shape: Ovoid; pointed. Color: Close to 45A and 53A.

*Petals*.—Quantity and arrangement: Five per flower in a single whorl. Length, banner petal: About 3 cm. Length, lateral and lower petals: About 3.5 cm. Width, banner petal: About 5.5 cm. Width, lateral and lower petals: About 3.5 cm. Shape, all petals: Cordate. Apex, all petals: Emarginate. Base, all petals: Attenuate. Margin, all petals: Entire. Texture, all petals, upper and lower surfaces: Smooth, glabrous. Color, banner petal: When opening and fully opened, upper surface: Close to 45A; color does not change with development. When opening and fully opened, lower surface: Close to 44A. Color, lateral and lower petals: When opening and fully opened, upper surface: Close to 45A; color does not change with development. When opening and fully opened, lower surface: Close to 44A; central longitudinal stripe, close to 45A.

*Sepals*.—Quantity and arrangement: Three; two lateral sepals and the third modified with an elongated spur. Length, lateral sepals: About 1.4 cm. Length, spurred sepal: About 1.7 cm. Length, spur: About 5.5 cm. Width, lateral sepals: About 7 mm. Width, spurred sepal: About 1.5 cm. Diameter, spur: About 2 mm. Shape, lateral sepals: Ovate. Shape, spurred sepal: Broadly ovate with elongated spur. Apex, all sepals: Acuminate. Base, all sepals: Cuneate. Margin, all sepals: Entire. Texture, all sepals, upper and lower surfaces: Smooth, glabrous. Color, immature: All sepals, upper surface: Close to and between 45A and 48D. All sepals, lower surface: Close to and between 45B and 48D. Spur, upper and lower surfaces: Close to 60A. Color, mature: Lateral sepals, upper surface: Close to 44A; apex, close to 144B. Lateral sepals, lower surface: Close to 60A. Spurred sepal, upper surface: Close to and between 45A and 48D. Spurred sepal, lower surface: Close to and between 45B and 48D. Spur, upper and lower surfaces: Close to 60A.

*Peduncles*.—Length: About 6.5 cm. Diameter: About 2 mm. Angle: Mostly erect. Strength: Moderately strong. Texture: Smooth, glabrous. Color: Close to 144B heavily tinted with close to 182A.

*Reproductive organs*.—Stamens: Quantity: Five fused at anthers; filaments free. Anther length: About 2 mm. Anther color: Close to 158B and 45A. Pollen amount: Moderate. Pollen color: Close to 158D. Pistils: Quantity per flower: One. Pistil length: About 0.5 mm. Stigma shape: Capitate. Stigma color: Close to 181C. Ovary color: Close to 146D and 187B.

*Seeds and fruits*.—Seed and fruit production have not been observed on plants of the new *Impatiens* plant.

Disease & pest resistance: Plants of the new *Impatiens* have not been observed to be resistant to pathogens and pests common to *Impatiens* plants.

Garden performance: Plants of the new *Impatiens* have been observed to have good garden performance and tolerate wind, rain and temperatures ranging from about 4° C. to about 35° C.

It is claimed:

1. A new and distinct *Impatiens* plant named 'Fidimpmaxred' as illustrated and described.

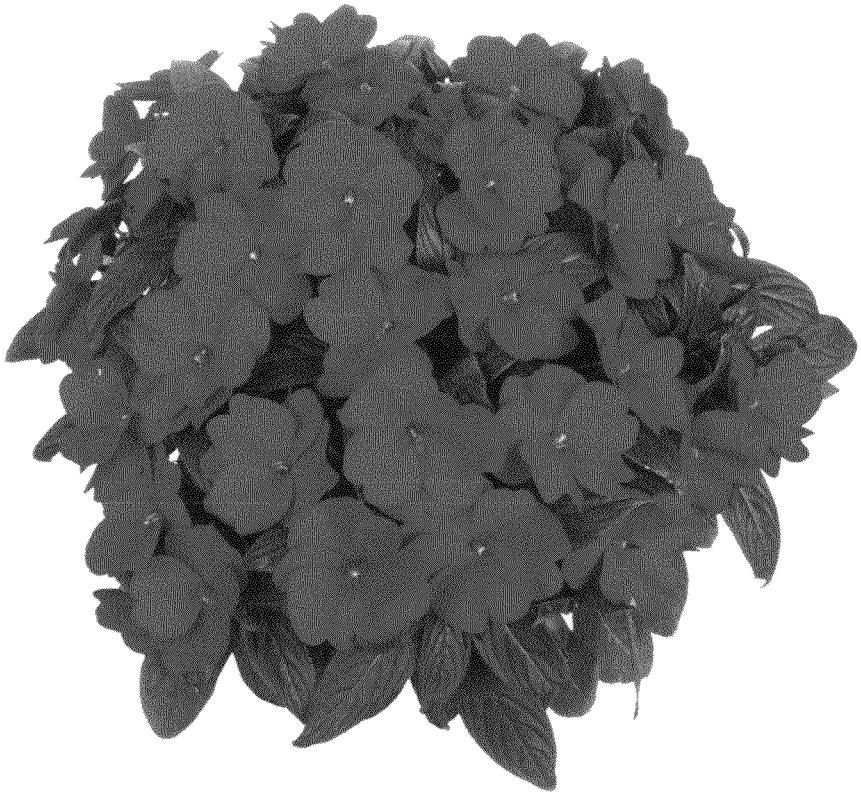

* * * * *